United States Patent [19]

Obikawa et al.

[11] Patent Number: 5,200,110
[45] Date of Patent: Apr. 6, 1993

[54] PYRIMIDINE DERIVATIVES AND LIQUID CRYSTAL COMPOSITIONS INCLUDING SAME

[75] Inventors: Tsuyoshi Obikawa; Shuhei Yamada; Shuji Ikukawa, all of Suwa, Japan

[73] Assignee: Seiko Epson Corporation, Tokyo, Japan

[21] Appl. No.: 870,727

[22] Filed: Apr. 15, 1992

Related U.S. Application Data

[63] Continuation of Ser. No. 501,203, Mar. 29, 1990, abandoned.

[30] Foreign Application Priority Data

| Apr. 6, 1989 | [JP] | Japan | 1-87428 |
| Apr. 6, 1989 | [JP] | Japan | 1-87429 |
| Sep. 11, 1989 | [JP] | Japan | 1-234896 |
| Oct. 12, 1989 | [JP] | Japan | 1-265665 |
| Nov. 20, 1989 | [JP] | Japan | 1-301451 |

[51] Int. Cl.$^5$ .................. C09K 19/34; C07C 277/00; C07C 255/00
[52] U.S. Cl. .................. 252/299.61; 544/242; 558/418
[58] Field of Search .......... 252/299.01, 299.61, 252/299.63; 544/242, 335; 558/418

[56] References Cited

U.S. PATENT DOCUMENTS

| 4,713,197 | 12/1987 | Eidenschink et al. | 252/299.61 |
| 4,818,428 | 4/1989 | Scheuble et al. | 252/299.61 |
| 4,834,904 | 5/1989 | Krause et al. | 252/299.61 |
| 4,883,609 | 11/1989 | Yamada | 252/299.61 |
| 5,030,382 | 7/1991 | Yamada | 252/299.61 |

FOREIGN PATENT DOCUMENTS

| 3411571 | 10/1985 | Fed. Rep. of Germany | 252/299.61 |
| WO86/04081 | 7/1986 | PCT Int'l Appl. | |

*Primary Examiner*—Robert L. Stoll
*Assistant Examiner*—Philip Tucker
*Attorney, Agent, or Firm*—Blum Kaplan

[57] ABSTRACT

2-phenyl-5-(4'-trans-cyclohexyl) phenyl pyrimidine derivatives represented by the general formula:

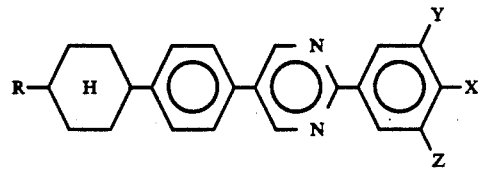

wherein R is a straight chain alkyl group having 1 to 10 carbon atoms; X is CN or F; Y is F or H; Z is F or H; and when X is F, at least one of Y and Z is H; and the cyclohexane ring is a trans isomer, exhibiting a nematic phase and having a high nematic phase-isotropic liquid phase transition temperature (N-I Point) and large positive dielectric constant anisotropy ($\Delta\epsilon$). The pyrimidine derivatives may be included in liquid crystal compositions for improved display devices having a wide temperature range, including a high N-I point, a low threshold voltage and a low driving voltage.

20 Claims, No Drawings

PYRIMIDINE DERIVATIVES AND LIQUID CRYSTAL COMPOSITIONS INCLUDING SAME

This is a continuation of application Ser. No. 07/501,203, filed Mar. 29, 1990 now abandoned.

BACKGROUND OF THE INVENTION

This invention relates to 2-phenyl-5-(4'-trans-cyclohexyl) phenyl pyrimidine derivatives, and more particularly to novel liquid crystal compositions including 2-phenyl-5-(4'-trans-cyclohexyl) phenyl pyrimidine derivatives suitable for use in electro-optical displays.

Liquid crystal display devices utilize electro-optical effects possessed by liquid crystals. The liquid crystal materials used in these devices have a nematic phase, a cholesteric phase and a smectic phase. The most widely used display mode uses liquid crystal materials in the nematic phase and include the dynamic scattering type (DSM), guest-host type (G-H), twisted nematic type (TN), super-twisted nematic type (STN), super-twisted birefringence (SBE) modes and the like. The driving systems used for these liquid crystal display devices include the static driving system, time driving system (Dynamic Driving System), active matrix driving system, two frequency driving system and the like.

Liquid crystal display devices have several advantages, particularly when compared with conventional light emission type displays including LED devices, EL devices and CRT devices. The devices are small in size and can be made thin, can be driven at low voltage with low power consumption, and show good compatibility with LSI and simple driving circuits. The liquid crystal material is a light receiving element so that when a liquid crystal display is viewed over a long time, eye strain does not occur.

In view of these benefits, liquid crystal display technology has been applied to watches, cameras, electronic counters, audio equipment, automobile dashboard indicators, electronic games, telephone equipment, measuring devices, and the like. More particularly, liquid crystal display devices have also been utilized recently in other devices including displays which require high resolution and many pixels.

The predominant liquid crystal display device is a TN type utilizing a time sharing driving system. However, the maximum number of scanning lines is about 200 and attempts to increase this number have been unsuccessful. In order to increase the number of scanning lines, STN mode liquid crystal display devices and TN mode liquid crystal display devices driven by active matrix driving systems have been used. The STN mode is currently utilized in liquid crystal display devices in personal computers and word processors, while TN mode devices driven by active matrix driving systems are predominantly utilized in color televisions. Thus, liquid crystal display devices continue to attract attention as potentially replacing cathode ray tubes. As a result, liquid crystal display devices have been applied in various areas and it is likely that their use will be broadened further.

For practical use, liquid crystal compositions must possess the following characteristics:
1. The liquid crystal materials must be colorless and thermally, optically, electrically and chemically stable;
2. Have a wide nematic temperature range; and
3. The driving voltage be low.

Many liquid crystal materials possess the first of the above-desired properties, however, no single compound satisfies all of the remaining characteristics. Thus, liquid crystal compositions are formed of several different nematic liquid crystal compounds or liquid crystal compositions are obtained by mixing liquid crystal compounds with non-liquid crystal compound to obtain the desired properties.

In order to satisfy the property of a wide nematic range, a liquid crystal compound having an N-I Point as high as possible and an N-I Point as low as possible is required. In general, the liquid crystal compositions are eutectic mixtures in order to reduce the lower limit of the nematic liquid crystal temperature range as low as possible. The composition of the eutectic mixture composition can be made by setting the ratio between each of the components to a particular composition ratio.

In general, to raise the upper limit of the temperature range, compounds having a high N-I Point are used. These compounds include, for example:

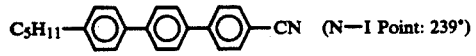

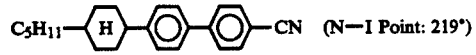

In order to decrease the driving voltage of a liquid crystal display device, it is necessary to decrease the threshold voltage. However, the following relationship exists between the threshold voltage ($V_{th}$), the thickness of the liquid crystal layer (d), the spray elasticity constant ($K_{11}$), the twist elasticity constant ($K_{22}$), the bend elasticity constant ($K_{33}$), dielectric constant anisotropy ($\Delta\epsilon$) and the dielectric constant in a vacuum ($\epsilon_0$):

$$V_{th} = \frac{\pi}{d} \sqrt{\frac{K_{11} + (k_{33} - 2K_{22})/4}{\epsilon_0 \Delta\epsilon}}$$

Thus, in order to decrease $V_{th}$, a liquid crystal compound having a large dielectric constant anisotropy ($\Delta\epsilon$) and a small elasticity constant is required. However, conventional compounds having a high N-I Point and large $\Delta\epsilon$ have very high elasticity constants which adversely effect $V_{th}$.

Accordingly, it is desirable to provide an improved liquid crystal material and composition having a wide temperature range and a low threshold voltage.

SUMMARY OF THE INVENTION

Generally speaking, in accordance with the invention, 2-phenyl-5-(4'-trans-cyclohexyl) phenyl pyrimidine derivatives represented by the general formula:

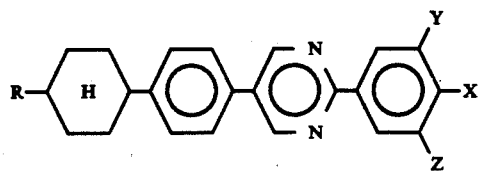

wherein R is a straight chain alkyl group having from 1 to 10 carbon atoms, X is F or CN, Y is H or F, Z is H or F, and when X is F, at least one of Y and Z is H, the cyclohexyl is the trans isomer and the compounds exhibit the nematic phase are provided. The 2-phenyl-5-(4'-trans-cyclohexyl) phenyl pyrimidine derivatives have high nematic phase - isotropic liquid phase transition temperatures (N-I Points) and large dielectric constant anisotropy (Δε). The 2-phenyl-5-(4'-trans-cyclohexyl) phenyl pyrimidine derivatives may be mixed with other liquid crystal compounds to obtain liquid crystal display devices having a wide temperature range and requiring a low driving voltage.

Accordingly, it is an object of the invention to provide an improved liquid crystal compound.

It is another object of the invention to provide 2-phenyl-5-(4'-trans-cyclohexyl) phenyl pyrimidine derivatives.

It is a further object of the invention to provide 2-phenyl-5-(4'-trans-cyclohexyl) phenyl pyrimidine derivatives having high N-I Points and large positive dielectric constant anisotropy (Δε).

Still another object of the invention is to provide 2-phenyl-5-(4'-trans-cyclohexyl) phenyl pyrimidine derivatives suitable for use in liquid crystal compositions for electro-optical display devices.

Still a further object of the invention is to provide improved liquid crystal compositions including 2-phenyl-5-(4'-trans-cyclohexyl) phenyl pyrimidine derivatives for improving the temperature range and lowering the driving voltage.

Yet a further object of the invention is to provide a method for preparing improved 2-phenyl-5-(4'-trans-cyclohexyl) phenyl pyrimidine derivatives.

Yet another object of the invention is to provide improved iquid crystal display devices including the liquid crystal compositions including 2-phenyl-5-(4'-trans-cyclohexyl) phenyl pyrimidine derivatives.

Still other objects and advantages of the invention will in part be obvious and will in part be apparent from the specification.

The invention accordingly comprises of several steps and the relation of one or more of such steps with respect to each of the others thereof, which will be exemplified in the composition, method and device hereinafter disclosed, and the scope of the invention will be indicated in the claims.

DESCRIPTION OF THE PREFERRED EMBODIMENTS

The liquid crystal compounds prepared in accordance witn the invention are 2-phenyl-5-(4'-trans-cyclohexyl) phenyl pyrimidine derivatives represented by the general formula as follows:

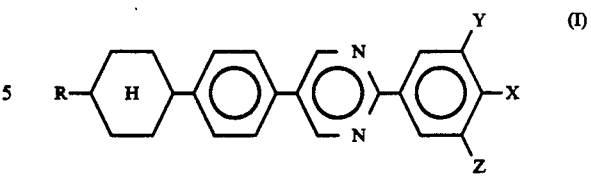

wherein R is a straight chain alkyl group having from 1 to 10 carbon atoms, X is F or CN, Y is H or F, Z is H or F, and when X is F, at least one of Y and Z is H, the cyclohexane ring is the trans isomer and the compounds exhibit the nematic phase.

The 2-phenyl-5-(4'-trans-cyclohexyl) phenyl pyrimidine compounds of this invention represented by the following general formulae II to VI have high N-I Points, as shown in Table 1. The compounds also have positive large dielectric constant anisotropy, particularly compounds III, and IV.

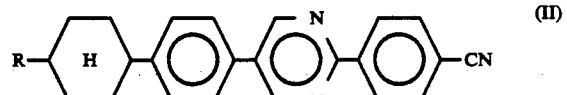

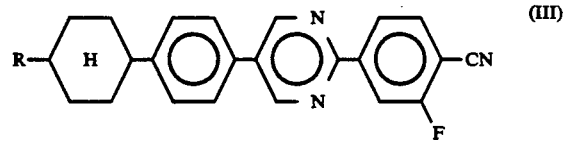

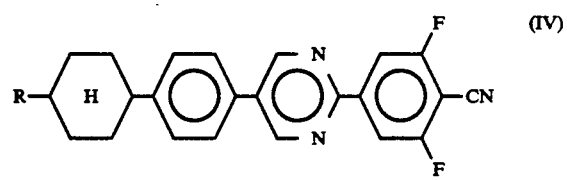

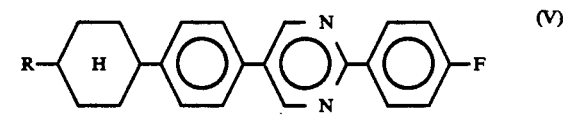

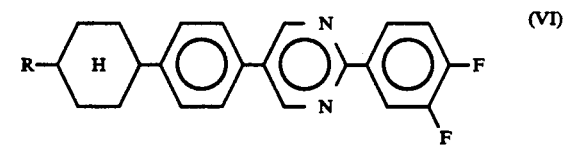

TABLE 1

| Compound | (N-I) point (°C.) |
|---|---|
| C₅H₁₁—⟨H⟩—⟨⟩—⟨N⟩—⟨⟩—CN | >360 |
| C₅H₁₁—⟨H⟩—⟨⟩—⟨N⟩—⟨⟩—CN, F | 346.5 |

TABLE 1-continued

| Compound | (N-I) point (°C.) |
|---|---|
| $C_5H_{11}$—[H]—[⎔]—[pyrimidine]—[C₆H₂F₂CN] | 307.7 |
| $C_5H_{11}$—[H]—[⎔]—[pyrimidine]—[C₆H₄F] | 316.9 |
| $C_5H_{11}$—[H]—[⎔]—[pyrimidine]—[C₆H₃F₂] | 287.7 |

Where the pyrimidine derivatives prepared in accordance with the invention are mixed with conventional liquid crystal compounds or with analogues thereof, the resulting compositions have a high upper limit of the temperature range and a low driving voltage. In general, the pyrimidines can be included in a conventional liquid crystal composition from about 1 to 30% by weight, preferably from about 3 and 20% by weight, in order to avoid crystallization at low temperatures. The pyrimidine derivatives in accordance with the invention are compatible with many liquid crystal materials, including the compounds listed below in Table 2, in addition to the compounds described in Composition Example 1.

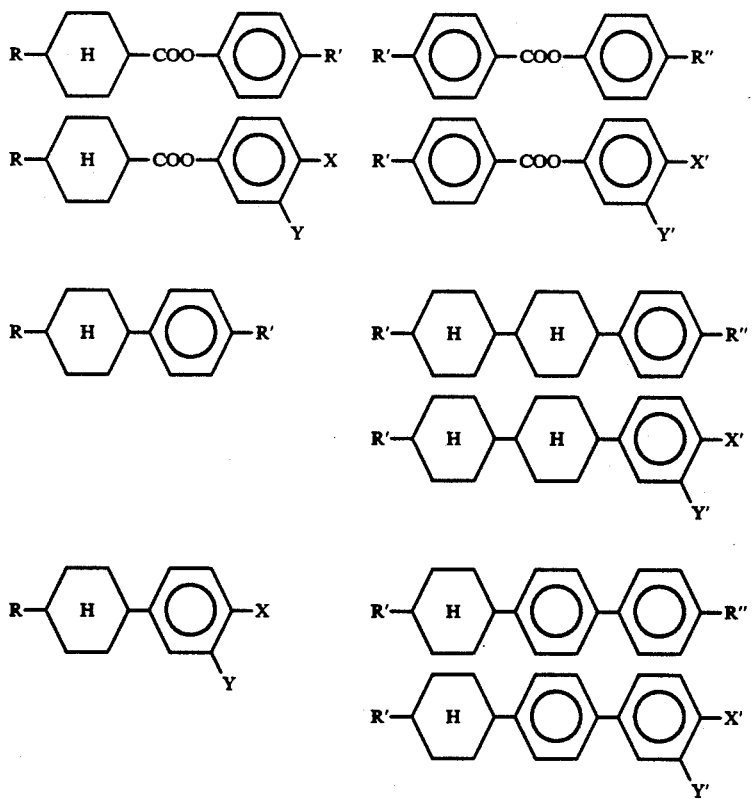

TABLE 2

TABLE 2-continued

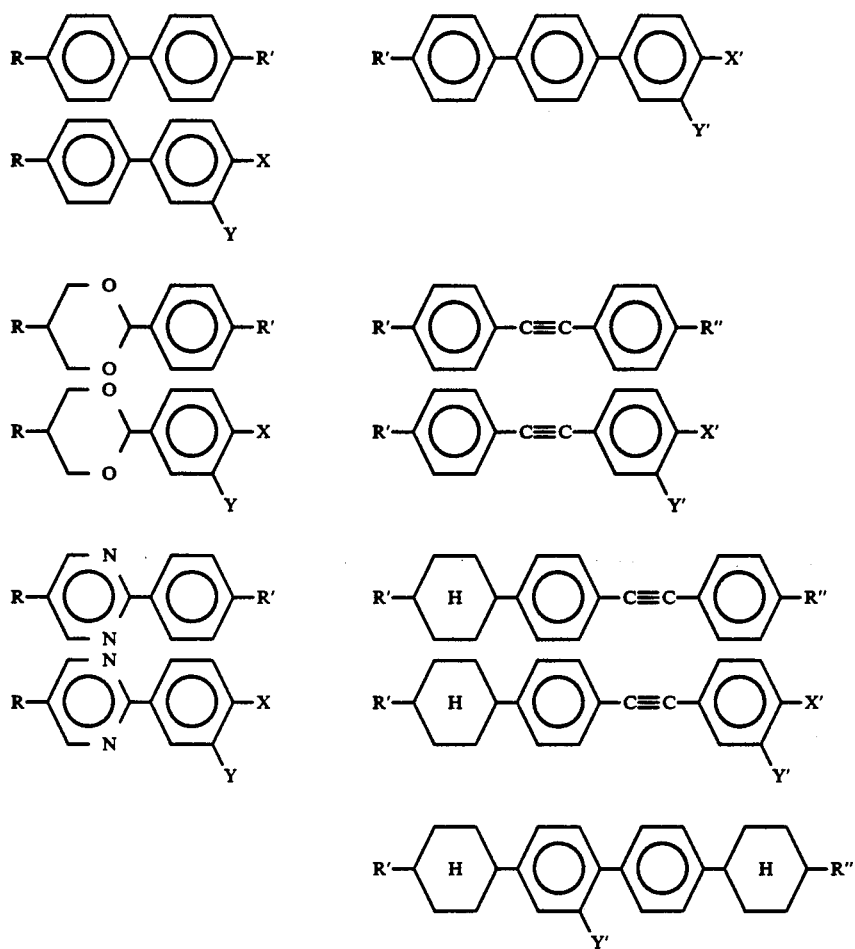

In addition when the pyrimidine derivatives in accordance with the invention are mixed with conventional liquid crystal compositions, a liquid crystal composition having a high N-I Point and a low driving voltage can be obtained by mixing the pyrimidine derivative with one other liquid crystal compound. However, the desirable effects can be enhanced by mixing the pyrimidine derivative of the invention with several other liquid crystal compounds or non-liquid crystal compounds or a mixture thereof. In particular, if the pyrimidine derivative is added in excess of 10 wt %, it is desirable to use a number of different compounds to avoid compatibility problems.

The 2-phenyl-5-(4'-trans-cyclohexyl) phenyl pyrimidine derivatives wherein X is CN and Y and Z are H, can be produced by the following Reaction Scheme I:

REACTION SCHEME I

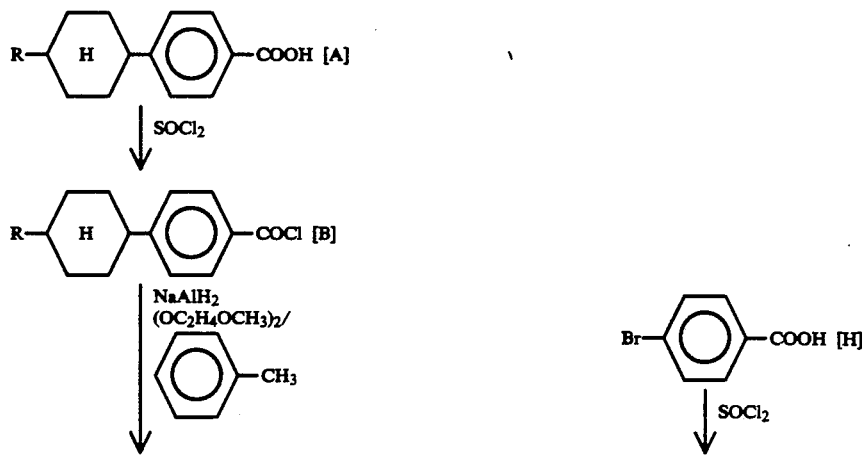

-continued
REACTION SCHEME I

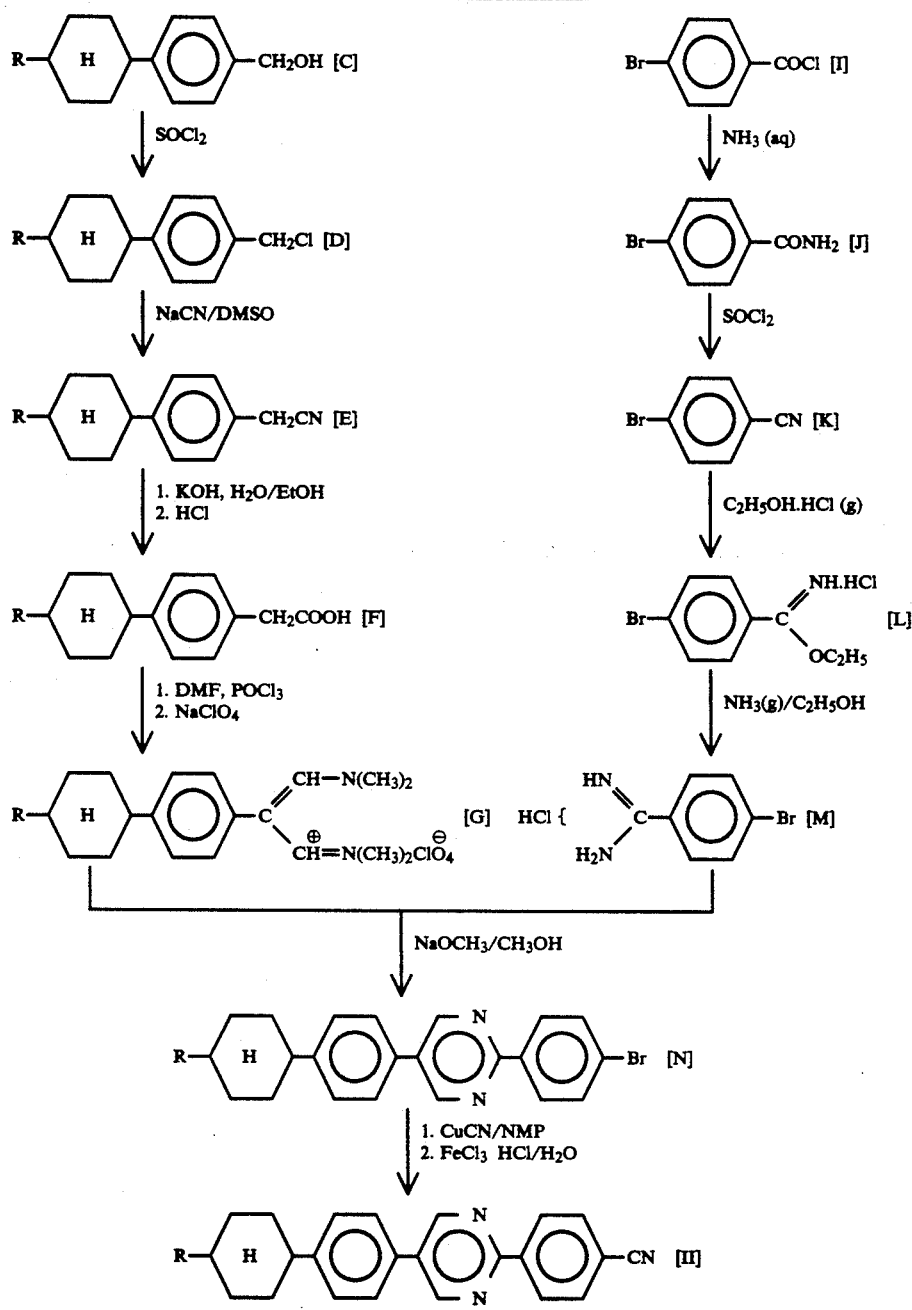

Compound [A], a 4-(trans-4'-alkylcyclohexyl) benzoic acid is chlorinated with thionyl chloride to yield compound [B], a 4-(trans-4'-alkylcyclohexyl) benzoic acid chloride. In toluene, compound [B] is reduced with sodium bis-(2-methoxyethoxy) aluminum hydride to yield compound [C], a 4-(trans-4'-alkylcyclohexyl) benzyl alcohol. Compound [C] is chlorinated with thionyl chloride to yield Compound [D], a 4-(trans-4'-alkylcyclohexyl) benzyl chloride. In dimethyl sulfoxide (DMSO), compound [D] is cyanated with sodium cyanate to yield compound [E], a 4-(trans-4'-alkylcyclohexyl)phenyl acetonitrile.

In ethanol, compound [E] is hydrolyzed with water and potassium hydroxide and neutralized with hydrogen chloride to yield compound [F], a 4-(trans-4'-alkylcyclohexyl)phenyl acetic acid. Compound [F] is reacted with a vilsmeier reagent, prepared by reacting N,N-dimethylformamide (DMF) with phosphorus oxychloride, and formed into a perchlorate with an aqueous solution of sodium perchlorate to yield compound [G], a 1-dimethylamino-3-dimethylimino-2-[4'-(trans-4'-alkylcyclohexyl)phenyl]-1-propene perchlorate.

Compound [H], 4-bromobenzoic acid is chlorinated with thionyl chloride to yield compound [I], 4-bromobenzoic acid chloride. Compound [I] is reacted with aqueous ammonia to yield compound [J] 4-bromobenzoic acid amide. Compound [J] is dehydrated with thionyl chloride to yield compound [K], a 4-bromobenzonitrile. Compound [K] is reacted with gaseous hydrogen chloride in anhydrous ethanol to yield compound [L], 4-bromobenzimidate hydrogen chloride. In ethanol, compound [L] is reacted with gaseous ammonia to yield compound [M], 4-bromobenzamidine hydrogen chloride.

Compound [G] and compound [M] are mixed in the presence of sodium methoxide in anhydrous methanol and the resultant copper complex is decomposed in a hydrochloric aid solution of iron (III) chloride to yield compound [N], a 2-(4'-bromophenyl)-5-[4'-(trans-4"-alkylcyclohexyl)phenyl]pyrimidine. In N-methyl-2-pyrrolidinone (NMP) compound [N] is cyanated with copper (I) cyanide and the complex formed is decomposed with a hydrochloric acid solution of iron (III) chloride to yield compound [II], a novel liquid crystal compound in accordance with the invention.

The 2-phenyl-5-(4'-trans-cyclohexyl) phenyl pyrimidine derivatives wherein X is CN and one of Y and Z is F, and the other of Y and Z is H can be produced by the following Reaction Scheme II:

REACTION SCHEME II

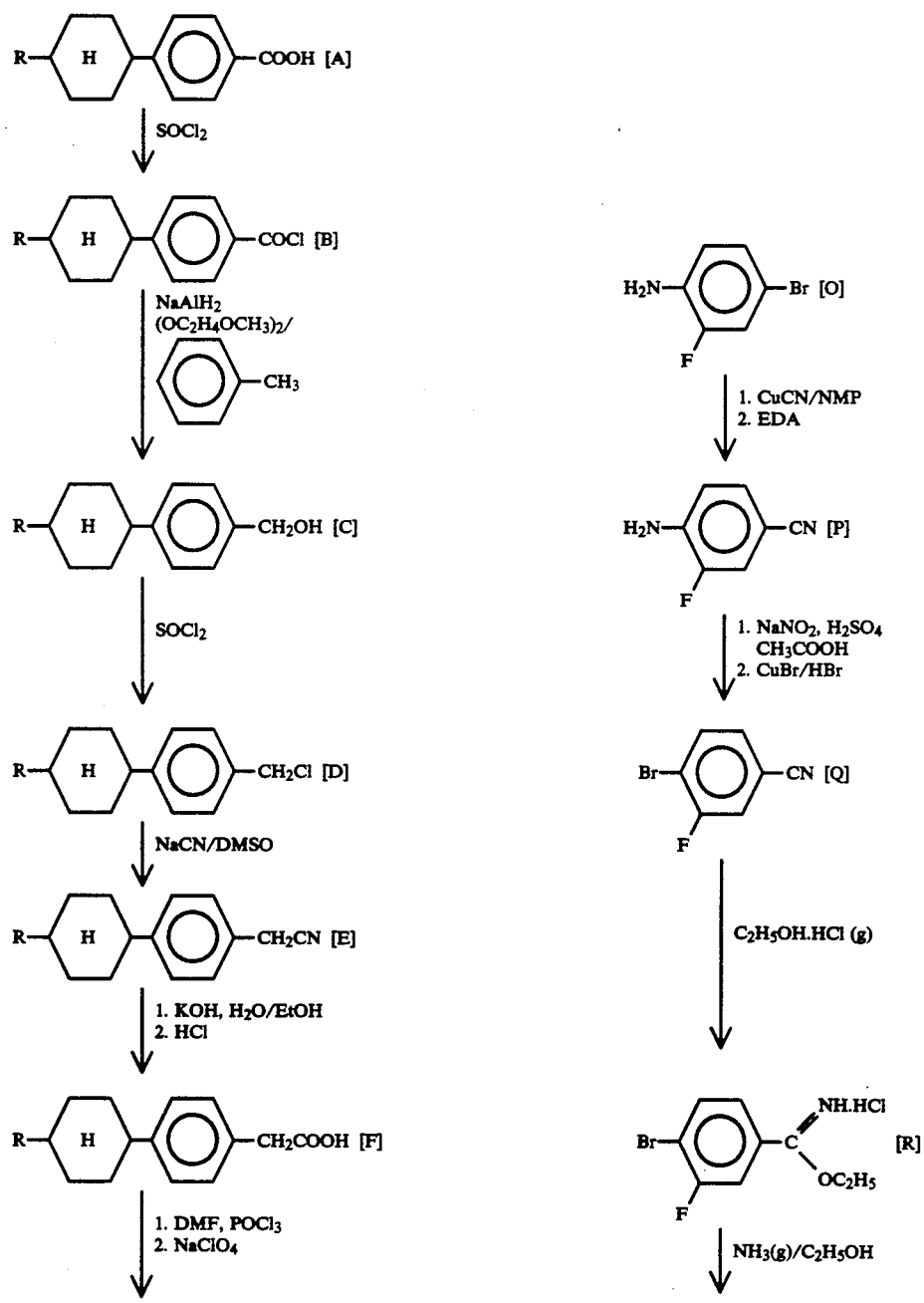

REACTION SCHEME II -continued

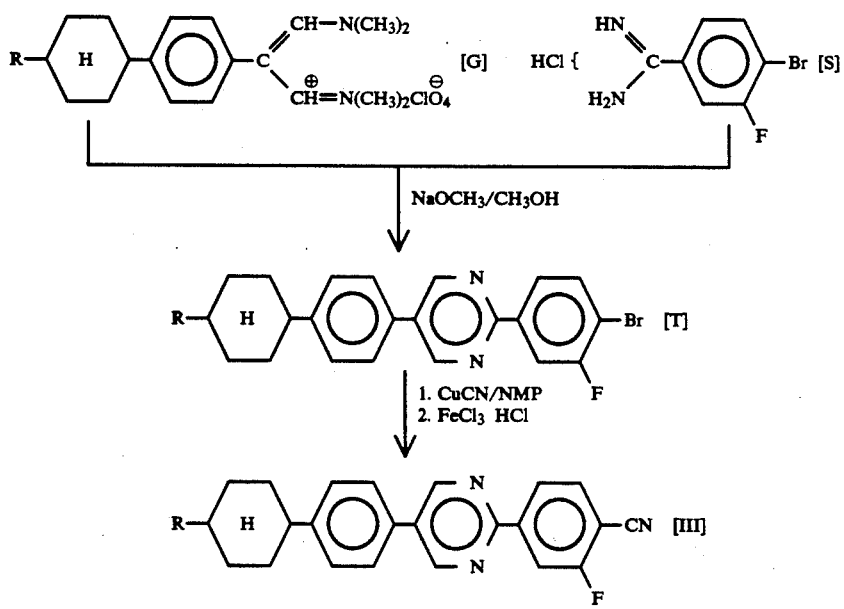

Compound [A], a 4-(trans-4'-alkylcyclohexyl) benzoic acid is chlorinated with thionyl chloride to yield compound [B], a 4-(trans-4'-alkylcyclohexyl) benzoic acid chloride. In toluene, compound [B] is reduced with sodium bis-(2-methoxyethoxy) aluminum hydride to yield compound [C], a 4-(trans-4'-alkylcyclohexyl) benzyl alcohol. Compound [C] is chlorinated with thionyl chloride to yield Compound [D], a 4-(trans-4'-alkylcyclohexyl) benzyl chloride. In dimethyl sulfoxide (DMSO), compound [D] is cyanated with sodium cyanate to yield compound [E], a 4-(trans-4'-alkylcyclohexyl)phenyl acetonitrile.

In ethanol, compound [E] is hydrolyzed with water and potassium hydroxide and neutralized with hydrogen chloride to yield compound [F], a 4-(trans-4'-alkylcyclohexyl)phenyl acetic acid. Compound [F] is reacted with a vilsmeier reagent, prepared by reacting N,N-dimethylformamide (DMF) with phosphorus oxychloride, and formed into a perchlorate with an aqueous solution of sodium perchlorate to yield compound [G], a 1-dimethylamino-3-dimethylimino-2-[4'-(trans-4'-alkylcyclohexyl)phenyl]-1-propene perchlorate.

In NMP, compound [O], commercially available 4-bromo-2-fluoroaniline is cyanated with copper (I) cyanide and the resulting copper complex is decomposed with ethylene diamine (EDA) to yield compound [P], 4-amino-3-fluorobenzonitrile. Compound [P] is reacted with nitrosyl hydrogen sulfate ($HSO_4$—$ONO_2$), prepared by mixing sodium nitrite and concentrated sulfuric acid in glacial acetic acid, and converted into the corresponding diazonium salt. The diazonium salt is brominated with copper (I) bromide in hydrobromic acid to yield compound [Q], 4-bromo-3-fluorobenzonitrile. Compound [Q] is reacted with gaseous hydrogen chloride in anhydrous ethanol to yield compound [R], 4-bromo-3-fluorobenzimidate hydrogen chloride. In ethanol, compound [R] is reacted with gaseous ammonia to yield compound [S], 4-bromo-3-fluorobenzamidine hydrogen chloride.

In anhydrous methanol, compound [G] and compound [S] are mixed with sodium methoxide to yield compound [T], 2-(4'-bromo-3'-fluorophenyl)-5-[4'-(trans-4''-alkylcyclohexyl)phenyl]pyrimidine. In NMP, compound [T] is cyanated with copper (I) cyanide to form a copper complex. The copper complex is decomposed in a hydrochloric acid solution of iron (III) chloride to yield compound [III], a novel liquid crystal compound in accordance with the invention.

The 2-phenyl-5-(4'-trans-cyclohexyl) phenyl pyrimidine derivatives wherein X is CN and Y and Z are F can be produced by the following Reaction Scheme III:

REACTION SCHEME III

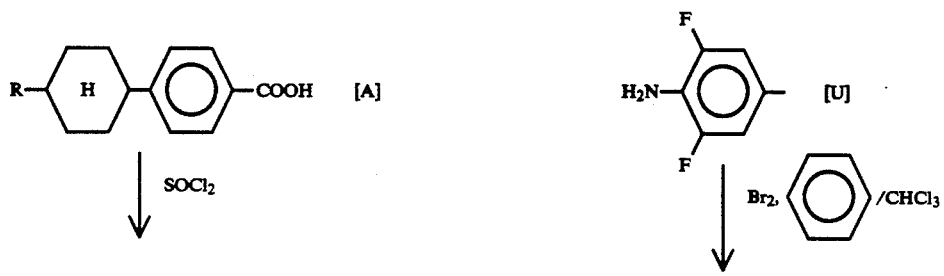

-continued
REACTION SCHEME III
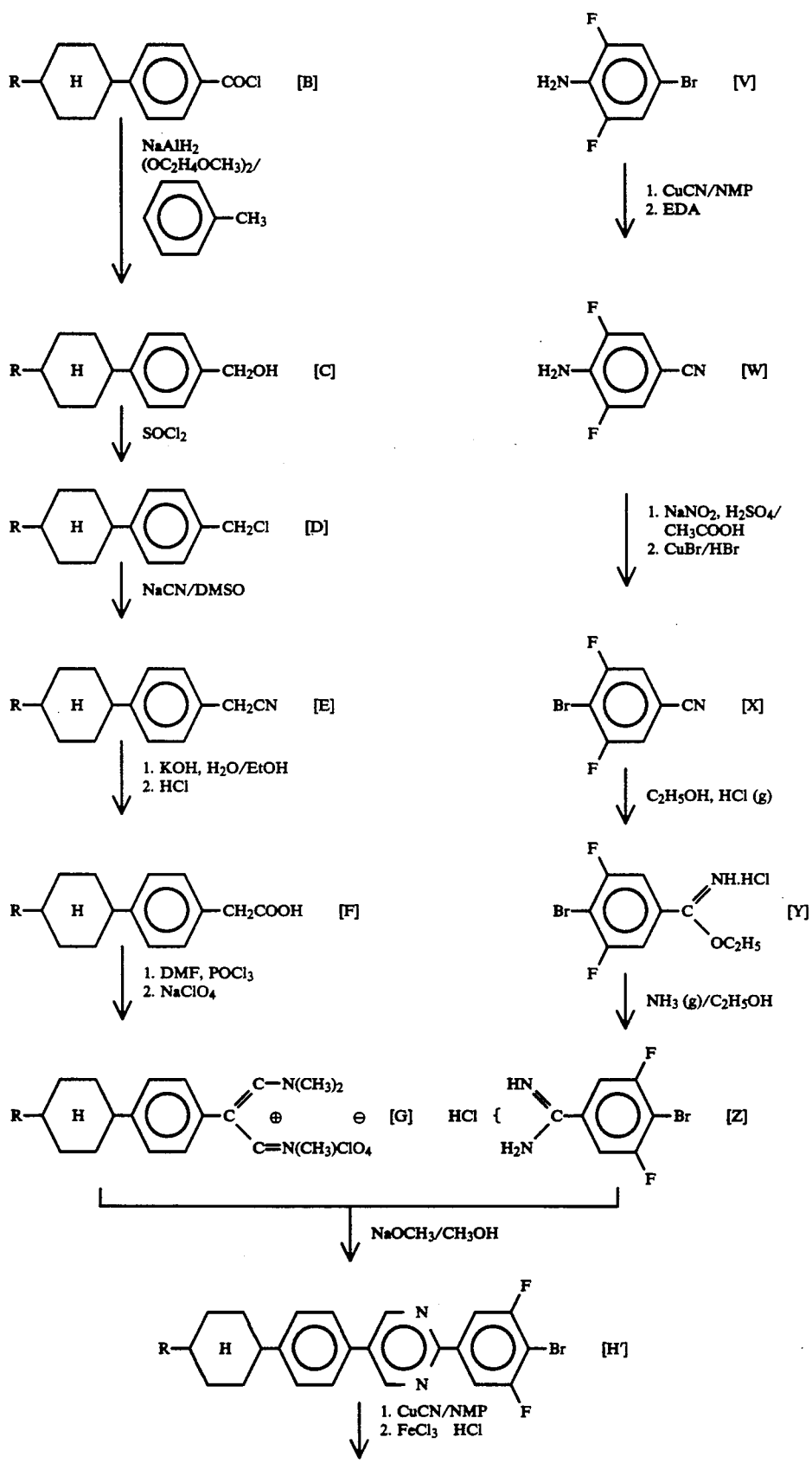

REACTION SCHEME III -continued

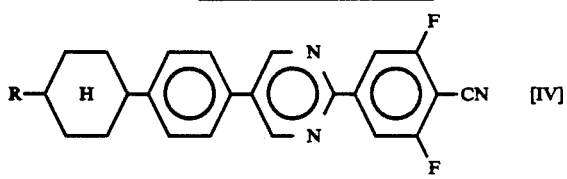

Compound [A], a 4-(trans-4'-alkylcyclohexyl) benzoic acid is chlorinated with thionyl chloride to yield compound [B], a 4-(trans-4'-alkylcyclohexyl) benzoic acid chloride. In toluene, compound [B] is reduced with sodium bis-(2-methoxyethoxy) aluminum hydride to yield compound [C], a 4-(trans-4'-alkylcyclohexyl) benzyl alcohol. Compound [C] is chlorinated with thionyl chloride to yield Compound [D], a 4-(trans-4'-alkylcyclohexyl) benzyl chloride. In dimethyl sulfoxide (DMSO), compound [D] is cyanated with sodium cyanate to yield compound [E], a 4-(trans-4'-alkylcyclohexyl)phenyl acetonitrile.

In ethanol, compound [E] is hydrolyzed with water and potassium hydroxide and neutralized with hydrogen chloride to yield compound [F], a 4-(trans-4'-alkylcyclohexyl)phenyl acetic acid. Compound [F] is reacted with a vilsmeier reagent, prepared by reacting N,N-dimethylformamide (DMF) with phosphorus oxychloride, and formed into a perchlorate with an aqueous solution of sodium perchlorate to yield compound [G], a 1-dimethylamino-3-dimethylimino-2-[4'-(trans-4'-alkylcyclohexyl)phenyl]-1-propene perchlorate.

In chloroform, commercially available compound [U], 2,6-difluoroaniline, is brominated with bromine in the presence of pyrimidine to yield compound [V], 4-bromo-2,6-difluoroaniline. In NMP, compound [V] is cyanated with copper (I) cyanide to form a copper complex. The copper complex is decomposed with EDA, to yield compound [W], 4-amino-3,5-difluorobenzonitrile. Compound [W] is converted into its corresponding diazonium salt with concentrated sulfuric acid in glacial acetic acid. In hydrobromic acid, the diazonium salt is brominated with copper (I) bromide to yield compound [X], 4-bromo-3,5-difluorobenzonitrile. Compound [X] is reacted with gaseous hydrogen chloride in anhydrous ethanol to yield compound [Y], 4-bromo-3,5-difluorobenzimidate hydrogen chloride. In ethanol, compound [Y] is reacted with gaseous ammonia to yield compound [Z], 4-bromo-3,5-difluorobenzamidine hydrogen chloride.

In anhydrous methanol, compound [G] and compound [Z] are mixed with sodium methoxide to yield compound [H'], a 2-(4'-bromo-3',5'-difluorophenyl)-5-[4'-(trans-4''-alkylcyclohexyl)phenyl]pyrimidine. In NMP, compound [H'] is cyanated with copper (I) cyanide to form a copper complex. The copper complex is decomposed in a hydrochloric acid solution of iron (III) chloride to yield compound [IV], a novel liquid crystal compound in accordance with the invention.

The 2-phenyl-5-(4'-trans-cyclohexyl) phenyl pyrimidine derivatives wherein X is F and Y and Z are H can be produced by the following Reaction Scheme IV:

REACTION SCHEME IV

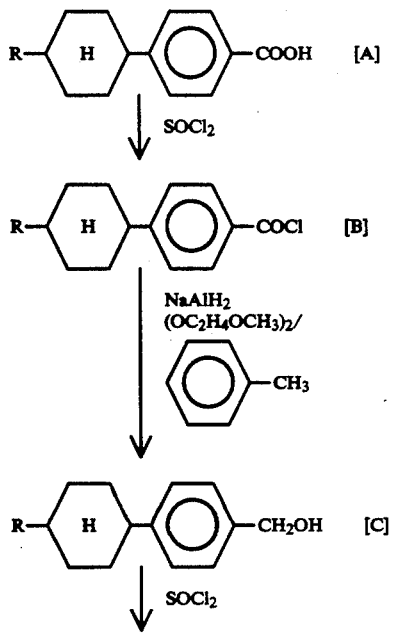

REACTION SCHEME IV -continued

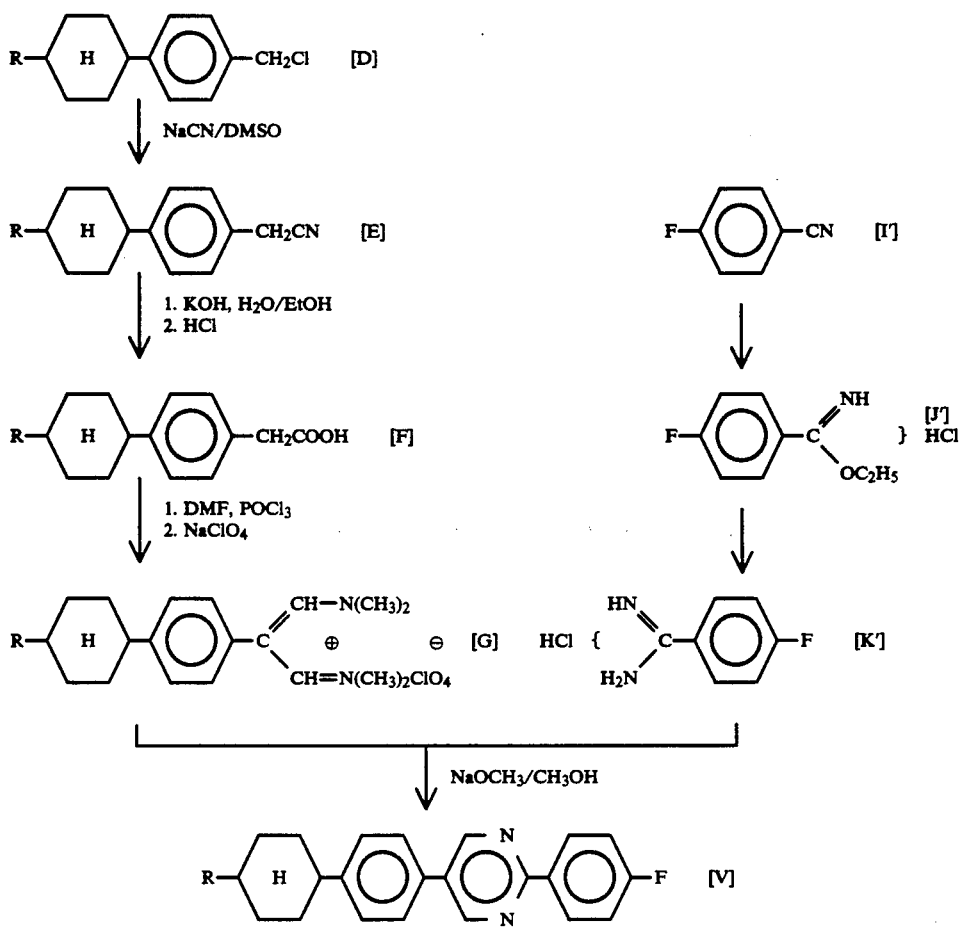

Compound [A], a 4-(trans-4'-alkylcyclohexyl) benzoic acid is chlorinated with thionyl chloride to yield compound [B], a 4-(trans-4'-alkylcyclohexyl) benzoic acid chloride. In toluene, compound [B] is reduced with sodium bis-(2-methoxyethoxy) aluminum hydride to yield compound [C], a 4-(trans-4'-alkylcyclohexyl) benzyl alcohol. Compound [C] is chlorinated with thionyl chloride to yield Compound [D], a 4-(trans-4'-alkylcyclohexyl) benzyl chloride. In dimethyl sulfoxide (DMSO), compound [D] is cyanated with sodium cyanate to yield compound [E], a 4-(trans-4'-alkylcyclohexyl)phenyl acetonitrile.

In ethanol, compound [E] is hydrolyzed with water and potassium hydroxide and neutralized with hydrogen chloride to yield compound [F], a 4-(trans-4'-alkylcyclohexyl)phenyl acetic acid. Compound [F] is reacted with a vilsmeier reagent, prepared by reacting N,N-dimethylformamide (DMF) with phosphorus oxychloride, and formed into a perchlorate with an aqueous solution of sodium perchlorate to yield compound [G], a 1-dimethylamino-3-dimethylimino-2-[4'-(trans-4'-alkylcyclohexyl)phenyl]-1-propene perchlorate.

In anhydrous ethanol, compound [I'], commercially available 4-fluorobenzonitrile is reacted with gaseous hydrogen chloride to yield compound [J'], 4-fluorobenzimidate hydrogen chloride. Compound [J'] is reacted with gaseous ammonia to yield compound [K'], 4-fluorobenzamidine hydrogen chloride.

In anhydrous methanol, compound [G] and compound [K'] are mixed with sodium methoxide to yield compound [V], a novel liquid crystal compound in accordance with the invention.

The 2-phenyl-5-(4'-trans-cyclohexyl) phenyl pyrimidine derivatives wherein X is F, one of Y and Z is F and the other of Y and Z is H can be produced by the following Reaction Scheme V:

REACTION SCHEME V

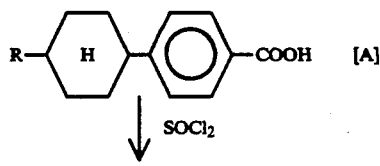

-continued
REACTION SCHEME V

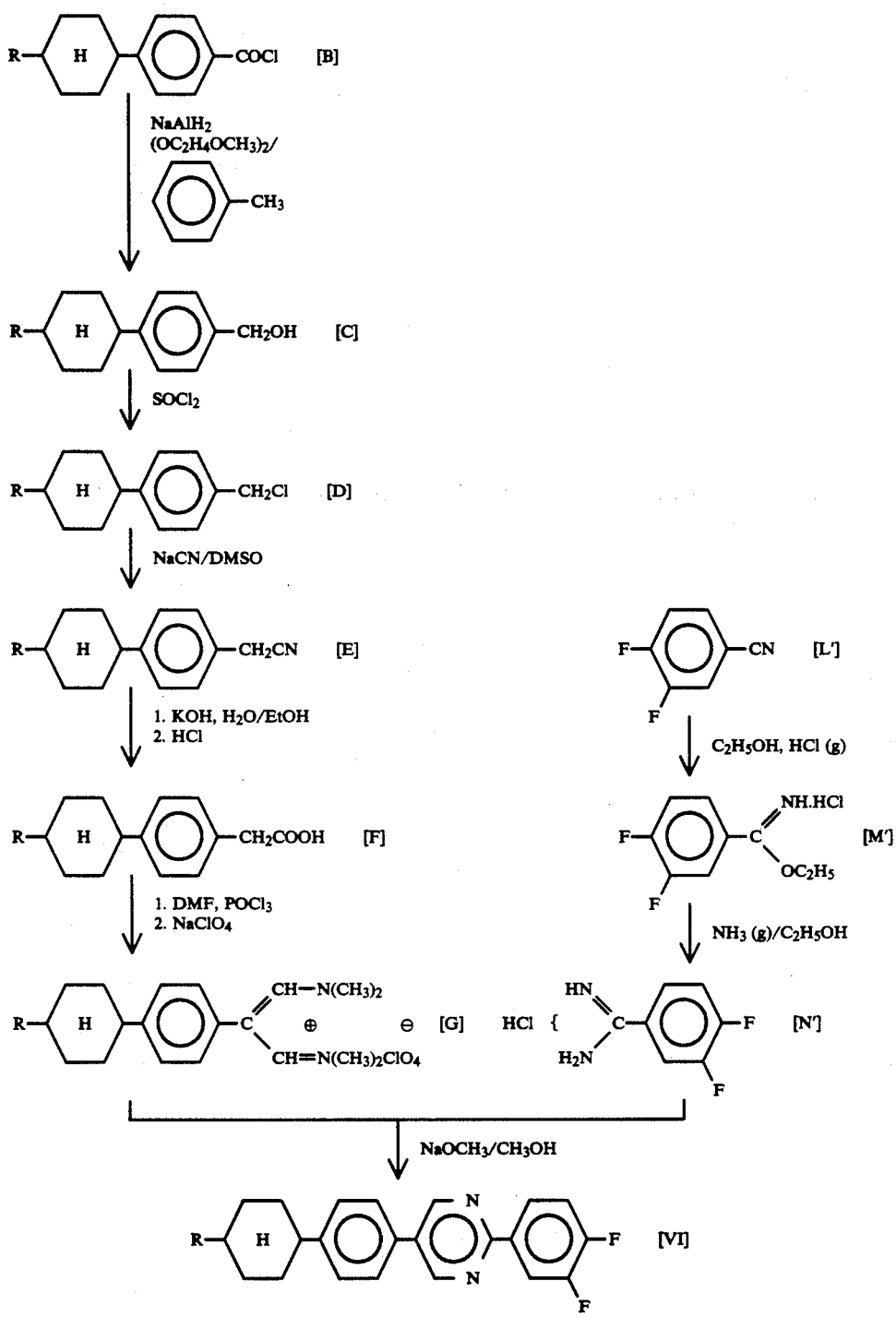

Compound [A], a 4-(trans-4'-alkylcyclohexyl) benzoic acid is chlorinated with thionyl chloride to yield compound [B], a 4-(trans-4'-alkylcyclohexyl) benzoic acid chloride. In toluene, compound [B] is reduced with sodium bis-(2-methoxyethoxy) aluminum hydride to yield compound [C], a 4-(trans-4'-alkylcyclohexyl) benzyl alcohol. Compound [C] is chlorinated with thionyl chloride to yield Compound [D], a 4-(trans-4'-alkylcyclohexyl) benzyl chloride. In dimethyl sulfoxide (DMSO), compound [D] is cyanated with sodium cyanate to yield compound [E], a 4-(trans-4'-alkylcyclohexyl)phenyl acetonitrile.

In ethanol, compound [E] is hydrolyzed with water and potassium hydroxide and neutralized with hydrogen chloride to yield compound [F], a 4-(trans-4'-alkylcyclohexyl)phenyl acetic acid. Compound [F] is reacted with a vilsmeier reagent, prepared by reacting N,N-dimethylformamide (DMF) with phosphorus oxychloride, and formed into a perchlorate with an aqueous solution of sodium perchlorate to yield compound [G], a 1-dimethylamino-3-dimethylimino-2-[4'-(trans-4'-alkylcyclohexyl)phenyl]-1-propene perchlorate.

In anhydrous ethanol, compound [L'], commercially available 3,4-difluorobenzonitrile is reacted with gaseous hydrogen chloride to yield compound [M'], 3,4-difluorobenzimidate hydrogen chloride. In ethanol, compound [M'] is reacted with gaseous ammonia to yield compound [N'], 3,4-difluorobenzamidine hydrogen chloride.

In anhydrous methanol, compound [G] and compound [N'] are mixed with sodium methoxide to yield compound [VI], a novel liquid crystal compound in accordance with the invention.

The following examples are set forth by way of illustration to show preparation of the 2-phenyl-5-(4'-trans-cyclohexyl) phenyl pyrimidine derivatives in accordance with the invention. They are set forth for purposes of illustration only, and are not intended in a limiting sense.

EXAMPLE 1

Preparation of 2-(4'-cyanophenyl)-5-[4'-(trans-4''-propylcyclohexyl) phenyl] pyrimidine:

Step 1:

In 75 cm$^3$ (1.0 mol) of SOCl$_2$, 128 g (0.52 mol) of 4-(trans-4'-propylcyclohexyl) benzoic acid was refluxed for 3 hours. The excess SOCl$_2$ was distilled off under a reduced pressure and the residue was distilled under reduced pressure (158° C./3.0 mmHg) to yield 133 g (0.50 mol) of 4-(trans-4'-propylcyclohexyl) benzoic acid chloride.

Step 2:

100 cm$^3$ of toluene was added to 170 cm$^3$ (0.6 mol) of 70% toluene solution of NaAlH$_2$(OC$_2$H$_4$OCH$_3$)$_2$. 133 g (0.50 mol) of 4-(trans-4'-propylcyclohexyl) benzoic acid chloride was added drop-wise to the solution while stirring at a rate to moderately reflux the toluene solution and the mixture was stirred over a warm water bath at a temperature of 88°-90° C. for 5 hours. The solution was cooled to room temperature and 500 cm$^3$ of concentrated hydrochloric acid diluted by twice its volume was added drop-wise. The toluene layer was separated out and the aqueous layer was extracted three times with 100 cm$^3$ of toluene. The toluene layers were combined and washed with 10% hydrochloric acid and water. The toluene was distilled off under reduced pressure and the residue was distilled under reduced pressure (150° C./2.5 mmHg) to yield 114 g (0.49 mol) of 4-(trans-4'-propylcyclohexyl) benzyl alcohol.

Step 3:

114 g (0.49 mol) of 4-(trans-4'-propylcyclohexyl) benzyl alcohol was dissolved in 107 cm$^3$ (1.05 mol) of SOCl$_2$ and the solution was refluxed over a warm water bath for 5 hours. The excess SOCl$_2$ was distilled off under reduced pressure and the residue was washed with 10% hydrochloric acid and water. The chloroform was distilled off under reduced pressure and the residue was distilled under reduced pressure (147° C./3.0 mmHg) to yield 114 g (0.45 mol) of 4-(trans-4'-propylcyclohexyl)-benzyl chloride.

Step 4:

114 g (0.45 mol) of 4-(trans-4'-propylcyclohexyl) benzyl chloride, 27 g (0.55 mol) of NaCN and 113 cm$^3$ of DMSO were mixed and while stirring, the mixture was heated to a temperature of 140° C. by a mantle heater. The product of the reaction was cooled to room temperature. 400 cm$^3$ of water was added and extracted three times with 100 cm$^3$ of chloroform. The chloroform layers were combined and washed with 10% hydrochloric acid and water. The chloroform was distilled off under reduced pressure and the residue was distilled under reduced pressure (155° C./2.5 mmHg) to yield 106 g (0.44 mol) of 4-(trans-4'-propylcyclohexyl) benzyl cyanide.

Step 5:

106 g (0.44 mol) of 4-(trans-4'-propylcyclohexyl) benzyl cyanide, 40 g of water, 145 g (2.2 mol) of KOH and 440 cm$^3$ of methanol were refluxed for 10 hours using a mantle heater. The ethanol was distilled off under reduced pressure. The residue was dissolved in 300 cm$^3$ of water and poured into 300 cm$^3$ of concentrated hydrochloric acid and 300 g of ice. The crystals deposited were filtered out and washed with cold water. The crystals were recrystallized from methanol to yield 112 g (0.43 mol) of 4-(trans-4'-propylcyclohexyl)-phenyl acetic acid.

Step 6:

A vilsmeier reagent was prepared by adding 197 g (1.3 mol) of POCl$_3$ drop-wise into 147 g (2.2 mol) of DMF while stirring over ice. 112 g (0.43 mol) of 4-(trans-4'-propylcyclohexyl)phenyl acetic acid powder was slowly added to the solution. The mixture was stirred on a warm water bath at a temperature of 70°-80° C. for three hours. The DMF was distilled off under reduced pressure using a vacuum pump, and the residue was poured onto 400 g of ice and dissolved by stirring. A solution containing 96 g (0.8 mol) of NaClO$_4$ dissolved in 150 cm$^3$ of water was added to the reaction solution while stirring and cooled with ice water. The crystals deposited were filtered out and washed with ice water. The crystals were recrystallized from a solvent mixture of methanol and water to yield 160 g (0.37 mol) of 1-dimethylamino-3-dimethylimino-2-[4'-(trans-4''-propylcyclohexyl)phenyl]-1-propene perchlorate.

Step 7:

101 g (0.5 mol) of 4-bromobenzoic acid was refluxed in 73 cm$^3$ (1.0 mol) of SOCl$_2$ for 3 hours on a warm water bath. The excess SOCl$_2$ was distilled off under reduced pressure on the warm water bath using an aspirator to yield 108 g (0.49 mol) of 4-bromobenzoic acid chloride.

Step 8:

On an ice water bath, 108 g (0.49 mol) of 4-bromobenzoic acid chloride was added drop-wise over 30 minutes to 330 cm$^3$ (4.9 mol) of concentrated aqueous ammonia while vigorously stirring. The resultant crystals were filtered out, washed with water and recrystallized from acetone to yield 88 g (0.44 mol) of 4-bromobenzoic acid amide.

Step 9:

88 g (0.44 mol) of 4-bromobenzoic acid amide and 320 cm$^3$ (4.4 mol) of SOCl$_2$ were refluxed on a warm water bath for 10 hours. The excess SOCl$_2$ was distilled off on warm water bath under reduced pressure using an aspirator and the residue was reorystallized from methanol to yield 67 g (0.37 mol) of 4-bromobenzonitrile.

Step 10:

Over an ice water bath, 67 g (0.37 mol) of 4-bromobenzonitrile was dissolved in 93 cm$^3$ of anhydrous benzene and 73 cm$^3$ of anhydrous ethanol, saturated with gaseous hydrogen chloride dried with concentrated sulfuric acid, while stirring. The solution was maintained at a temperature below 5° C. for two days in a tightly sealed reaction vessel. The solvent was distilled off under reduced pressure and the residue was recrystallized from ethanol to yield 86 g (0.32 mol) of 4-bromobenzimidate hydrogen chloride.

Step 11:

86 g (0.32) of 4-bromobenzimidate hydrogen chloride was added to 240 cm³ of ethanol saturated with gaseous ammonia and stirred at room temperature overnight. Approximately one-half of the volume of the ethanol was distilled off and the residual solution was recrystallized to yield 57 g (0.24 mol) of 4-bromobenzamidine hydrogen chloride.

Step 12:

6.9 (0.03 mol) of sodium was dissolved in 100 cm³ of anhydrous methanol. 4.3 g (0.01 mol) of 1-dimethylamino-3-dimethylimino-2-[4'-(trans-4"-propylcyclohexyl)phenyl]-1-propene perchlorate and 3.5 g (0.015 mol) of 4-bromobenzamidine hydrogen chloride were added to the solution and the solution was maintained on a warm water bath at a temperature of 60° C. for 5 hours. The methanol was distilled off and the residue was extracted with chloroform with the addition of water and washed with water. The chloroform was distilled off and the residue was recrystallized from chloroform to yield 3.3 g (0.008 mol) of 2-(4'-bromophenyl)-5-[4'-(trans-4'-propylcyclohexyl)phenyl]-pyrimidine.

Step 13:

3.3 g of 2-(4'-bromophenyl)-5-[4'-(trans-4"-propylcyclohexyl)phenyl]pyrimidine and 0.9 g (0.01 mol) of CuCN were added to 30 cm³ of NMP and the solution was refluxed for 2 hours using a mantle heater. The solution was cooled to 60° C. and added to a solution of 4.4 g of FeCl₃.6H₂O, 1.3 cm³ of concentrated hydrochloric acid and 6 cm³ of water. The resulting solution was heated on a warm water bath at a temperature of 60° C. for one hour. The crystals deposited were filtered out, washed with water and treated through a silica gel column using chloroform as the solvent. The chloroform was distilled off and the residue was recrystallized from a mixture of acetone and chloroform to yield 2.2 g (0.006 mol) of 2-(4'-cyanophenyl)-5-[4'-(trans-4"-propylcyclohexyl) phenyl] pyrimidine. The phase transition temperature of this compound, measured by DSC, was:

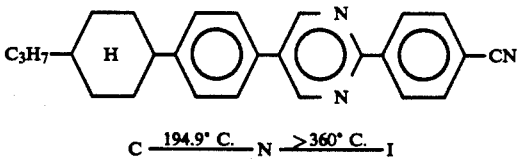

C —— 194.9° C. —— N —— >360° C. —— I wherein C is the crystal phase, N is the nematic phase and I is the isotropic liquid phase.

The following are other examples of the compounds in accordance with the invention prepared following the procedures of Example 1:

2-(4'-cyanophenyl)-5-[4'-(trans-4"-methylcyclohexyl) phenyl] pyrimidine 2-(4'-cyanophenyl)-5-[4'-(trans-4"-ethylcyclohexyl) phenyl] pyrimidine

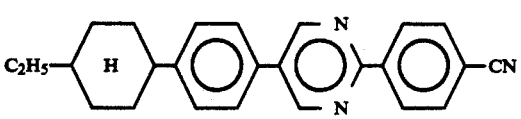

C —— 210.5° C. —— N —— >360° C. —— I 2-(4'-cyanophenyl)-5-[4'-(trans-4"-butylcyclohexyl) phenyl] pyrimidine

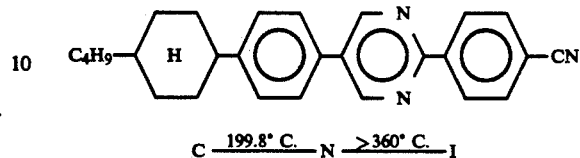

C —— 199.8° C. —— N —— >360° C. —— I 2-(4'-cyanophenyl)-5-[4'-(trans-4"-pentylcyclohexyl) phenyl] pyrimidine

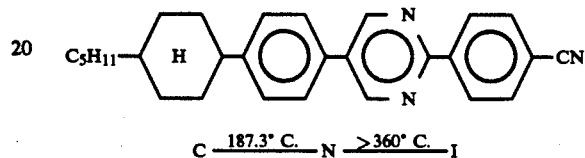

C —— 187.3° C. —— N —— >360° C. —— I 2-(4'-cyanophenyl)-5-[4'-(trans-4"-hexylcyclohexyl) phenyl] pyrimidine 2-(4'-cyanophenyl)-5-[4'-(trans-4"-heptylcyclohexyl) phenyl] pyrimidine 2-(4'-cyanophenyl)-5-[4'-(trans-4"-octylcyclohexyl) phenyl] pyrimidine 2-(4'-cyanophenyl)-5-[4'-(trans-4"-nonylcyclohexyl) phenyl] pyrimidine 2-(4'-cyanophenyl)-5-[4'-(trans-4"-decylcyclohexyl) phenyl] pyrimidine

EXAMPLE 2

Preparation of 2-(4'-cyano-3'-fluorophenyl)-5-[4'-(trans-4"-propylcyclohexyl)phenyl]pyrimidine:

Step 1 to Step 6:

1-dimethylamino-3-dimethylimino-2-[4'-(trans-4"-propylcyclohexyl)phenyl]-1-propene perchlorate was prepared in the same manner as in Steps 1 through 6 of Example 1.

Step 7:

100 g (0.53 mol) of 4-bromo-fluoroaniline (manufactured by Aldorich Co.) and 70.8 g (0.79 mol) of copper (I) cyanide was refluxed in N-methyl-2-pyrrolidinone for three hours while stirring. The solution was cooled and a solution of 130 cm³ of ethylene diamine and 130 cm³ of water was added drop-wise while stirring. The solution was extracted three times with 200 cm³ of chloroform and sufficiently washed with water. The chloroform was distilled off and the residue was distilled under reduced pressure (150° C./9 mmHg) to yield 55 g (0.40 mol) of 4-amino-3-fluorobenzonitrile.

Step 8:

30.8 g (0.45 mol) of sodium nitrite was added slowly to 244 cm³ of concentrated sulfuric acid while stirring. After the addition was complete, the solution was heated to a temperature of 50° C. to dissolve the crystals. The solution was added drop-wise to 406 cm³ of acetic acid while cooling on an ice water bath and stirring. 55 g (0.40 mol) of 4-amino-3-fluorobenzonitrile was added slowly to maintain the temperature below 25° C. and the mixture was stirred at 25° C. for one hour to dissolve the crystals and form the corresponding diazonium salt. While cooling with ice water and stirring, the diazonium salt was added drop-wise to a solution of 87.4 g (0.61 mol) of copper (I) bromide and 244 cm³ of hydrobromic acid (47%) and allowed to remain overnight at room temperature. The crystals deposited were filtered out, washed with water and recrystallized from hexane to yield 61.7 g (0.31 mol) of 4-bromo-3-fluorobenzonitrile.

Step 9:

On an ice water bath, 61.7 g (0.31 mol) of 4-bromo-3-fluoro-benzonitrile was dissolved in 62 cm³ of ethanol and 78 cm³ of benzene saturated with gaseous hydrogen chloride dried with concentrated sulfuric acid. The solution was maintained at 5° C. for two days. The solvent was distilled off on a warm water bath under reduced pressure using an aspirator. 310 cm³ of ammonia-saturated ethanol was added to the residue and the mixture was stirred overnight at room temperature. The ethanol was distilled off over a warm water bath under reduced pressure. The residue was recrystallized from ethanol to yield 64.7 g (0.26 mol) of 4-bromo-3-fluorobenzamidine hydrogen chloride.

Step 10:

6.9 g (0.03 mol) of sodium was dissolved in 100 cm³ of methanol. 4.3 g (0.01 mol) of 1-dimethylamino-3-dimethylimino-2-[4′-(trans-4″-propylcyclohexyl)phenyl]-1-propene perchlorate and 3.1 g (0.012 mol) of 4-bromobenzamidine hydrogen chloride were added to the solution and the solution was maintained on a warm water bath at a temperature of 60° C. for 5 hours. The methanol was distilled off and the residue was extracted with chloroform with the addition of water and washed with water and the chloroform was distilled off. Water was added to the residue and crystals were filtered and washed with water. The crystals were recrystallized from chloroform to yield 3.3 g (0.008 mol) of 2-(4′-bromo-3′-fluorophenyl)-5-[4′-(trans-4″-propylcyclohexyl)phenyl]pyrimidine.

Step 11:

3.5 g (0.008 mol) of 2-(4′-bromo-3′-fluorophenyl)-5-[4′-(trans-4″-propylcyclohexyl)phenyl]pyrimidine and 1.1 g (0.012 mol) of copper (I) cyanide were added to 31 cm³ of NMP and the solution was refluxed for 2 hours using a mantle heater. The solution was cooled to 60° C. and added to a solution of 4.2 g of $FeCl_3 \cdot 6H_2O$, 1.3 cm³ of concentrated hydrochloric acid and 6 cm³ of water. The resulting solution was maintained on a warm water bath at 60° C. for one hour. The crystals deposited were filtered, washed with water and treated through a silica gel column with chloroform as the solvent. The chloroform was distilled off and the residue was recrystallized from acetone to yield 1.9 g (0.005 mol) of 2-(4′-cyano-3′-fluorophenyl)-5-[4′-(trans-4″-propylcyclohexyl)phenyl]pyrimidine. The phase transition temperature of this compound measured by DSC, was:

C $\xrightarrow{157.0° C.}$ N $\xrightarrow{362.7° C.}$ I

The following are other examples of compounds prepared in accordance with the invention following the procedures of Example 2:

2-(4′-cyano-3′-fluorophenyl)-5-[4′-(trans-4″-methylcyclohexyl) phenyl] pyrimidine 2-(4′-cyano-3′-fluorophenyl)-5-[4′-(trans-4″-ethylcyclohexyl) phenyl] pyrimidine C $\xrightarrow{173.0° C.}$ N $\xrightarrow{349.9° C.}$ I 2-(4′-cyano-3′-fluorophenyl)-5-[4′-(trans-4″-butylcyclohexyl) phenyl] pyrimidine C $\xrightarrow{159.2° C.}$ N $\xrightarrow{353.6° C.}$ I 2-(4′-cyano-3′-fluorophenyl)-5-[4′-(trans-4″-pentylcyclohexyl) phenyl] pyrimidine C $\xrightarrow{138.6° C.}$ S $\xrightarrow{145.2° C.}$ N $\xrightarrow{346.5° C.}$ I 2-(4′-cyano-3′-fluorophenyl)-5-[4′-(trans-4″-hexylcyclohexyl) phenyl] pyrimidine
2-(4′-cyano-3′-fluorophenyl)-5-[4′-(trans-4″-heptylcyclohexyl) phenyl] pyrimidine
2-(4′-cyano-3′-fluorophenyl)-5-[4′-(trans-4″-octylcyclohexyl) phenyl] pyrimidine
2-(4′-cyano-3′-fluorophenyl)-5-[4′-(trans-4″-nonylcyclohexyl) phenyl] pyrimidine
2-(4′-cyano-3′-fluorophenyl)-5-[4′-(trans-4″-decylcyclohexyl) phenyl] pyrimidine

EXAMPLE 3

Preparation of 2-(4′-cyano-3′,5′-difluorophenyl-5-[4′-(trans-4″-propylcyclohexyl)phenyl]pyrimidine:

Step 1 to Step 6:

1-dimethylamino-3-dimethylimino-2-[4′-(trans-4″-propylcyclohexyl)phenyl]-1-propene perchlorate was prepared in the same manner as in Steps 1 through 6 of Example 1.

Step 7:

328 g (2.05 mol) of bromine was dissolved in 390 cm³ of chloroform and added drop-wise, while stirring, to a solution of 252 g (1.95 mol) of 2,6-difluoroaniline and 170 g (2.15 mol) of anhydrous pyrimidine dissolved in 780 cm³ of chloroform, over 2 hours. The solution was stirred at room temperature for 2 hours and washed with water. The chloroform was distilled off and the residue was distilled under reduced pressure (110° C./30 mmHg). The crystals formed were recrystallized from hexane to yield 340 g (1.63 mol) of 4-bromo-2,6-difluoroaniline.

Step 8:

340 g (1.63 mol) of 4-bromo-2,6-difluoroaniline and 223 g (2.5 mol) of copper (I) cyanide were refluxed in 820 cm³ of NMP for 2 hours using a mantle heater. 300 cm³ of EDA, in 2000 cm³ of water was added to the solution and cooled to room temperature. The solution was extracted with hexane and washed with water. The hexane was distilled off and the residue was distilled under reduced pressure (143° C./6 mmHg) to yield 108 g (0.70 mol) of 4-amino-5-difluoro-benzonitrile.

Step 9:

While stirring 420 cm³ of concentrated sulfuric acid on an ice water bath, 54 g (0.78 mol) of finely pulverized NaNO₂ was added at a rate which maintained the temperature below 40° C. The mixture was stirred on a warm water bath at 50° C. until the crystals were completely dissolved. The solution was stirred on an ice water bath and 700 cm³ of glacial acetic acid was added drop-wise. 108 g (0.70 mol) of 4-amino-3,5-difluorobenzonitrile was added at a rate which maintained the temperature at 20°-25° C. and the mixture was stirred at that temperature until the crystals were completely dissolved to form the corresponding diazonium salt. An aqueous solution of the diazonium salt was added dropwise for 2 hours to a solution of 143 g (1.0 mol) of copper (I) bromide dissolved in 420 cm³ of 47% hydrobromic acid while stirring on an ice water bath. The resulting solution was stirred for one hour on an ice water bath and allowed to sit overnight at room temperature. The product was filtered, washed with glacial acetic acid and recrystallized from a solvent mixture of acetone and methanol to yield 98 g (0.45 mol) of 4-bromo-3,5-difluorobenzonitrile.

Step 10:

On an ice water bath, 98 g (0.45 mol) of 4-bromo-3,5-difluorobenzonitrile was dissolved in a solvent mixture of 190 cm³ of anhydrous ethanol and 600 cm³ of anhydrous benzene saturated with gaseous hydrogen chloride dried with concentrated sulfuric acid. The reaction vessel was tightly sealed and allowed to sit at a temperature below 5° C. for two days. The solvent was distilled off and the residue was washed with ether to yield 4-bromo-3,5-difluorobenzimidate hydrogen chloride.

Step 11:

450 cm³ of anhydrous ethanol saturated with dried gaseous ammonia was added to 4-bromo-3,5-difluorobenzimidate hydrogen chloride and stirred overnight at room temperature. About one-half of the volume of the solvent was distilled off and the residue was recrystallized to yield 90 g (0.36 mol) of 4-bromo-3,5-difluorobenzamidine hydrogen chloride.

Step 12:

0.69 g (0.03 mol) of sodium was dissolved in 100 cm³ of methanol. 4.3 g (0.01 mol) of 1-dimethylamino-3-dimethylimino-2-[4'-(trans-4''-propylcyclohexyl)-phenyl]-1-propene perchlorate and 4.1 g (0.015 mol) of 4-bromobenzamidine hydrogen chloride were added to the solution and the solution was allowed to sit on a warm water bath at a temperature of 60° C. for 5 hours. The methanol was distilled off and the residue was filtered with additional water and washed with water. The crystals formed were recrystallized from a solvent mixture of acetone and chloroform to yield 3.0 g (0.006 mol) of 2-(4'-bromo-3',5'-difluorophenyl)-5-[4'-(trans-4''-propylcyclohexyl)phenyl]pyrimidine.

Step 13:

3.0 g (0.006 mol) of 2-(4'-bromo-3',5'-difluorophenyl)-5-[4'-(trans-4''-propylcyclohexyl)phenyl]pyrimidine and 0.8 g (0.08 mol) of copper (I) cyanide were added to 30 cm³ of NMP and the solution was refluxed for 2 hours using a mantle heater. The solution was cooled to 60° C. and added to a solution of 3.2 g of FeCl₃.6H₂O, 1.0 cm³ of concentrated hydrochloric acid and 4 cm³ of water. The resulting solution was allowed to sit on a warm water bath at 60° C. for one hour. The crystals formed were filtered out, washed with water and treated through a silica gel column using chloroform as the solvent. The chloroform was distilled off and the residue was recrystallized from a solvent mixture of acetone and chloroform to yield 1.3 g (0.003 mol) of 2-(4'-cyano-3',5'-difluorophenyl)-5-[4'-(trans-4''-propylcyclohexyl)phenyl]pyrimidine. The phase transition temperature of this compound, as measured by DSC, was:

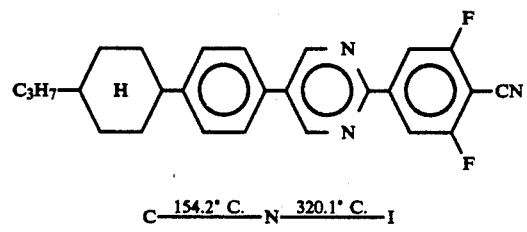

C ———154.2° C.——— N ———320.1° C.——— I

The following are other examples of compounds prepared in accordance with the invention following the procedures of Example 3:

2-(4'-cyano-3',5'-difluorophenyl)-5-[4'-(trans-4''-methylcyclohexyl) phenyl] pyrimidine 2-(4'-cyano-3',5'-difluorophenyl)-5-[4'-(trans-4''-ethylcyclohexyl) phenyl] pyrimidine

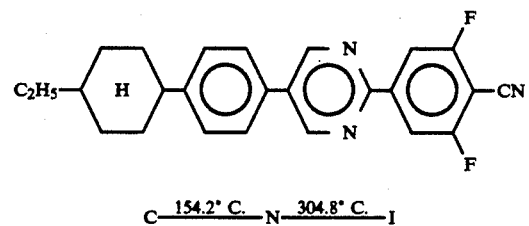

C ———154.2° C.——— N ———304.8° C.——— I 2-(4'-cyano-3',5'-difluorophenyl)-5-[4'-(trans-4''-butylcyclohexyl) phenyl] pyrimidine

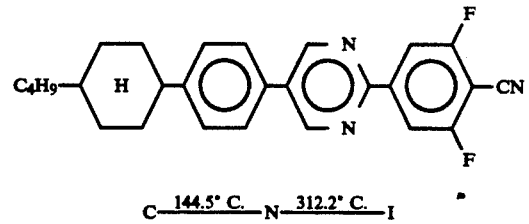

C ———144.5° C.——— N ———312.2° C.——— I 2-(4'-cyano-3',5'-difluorophenyl)-5-[4'-(trans-4''-pentylcyclohexyl) phenyl] pyrimidine

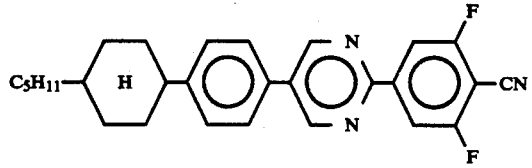

-continued

C —150.3° C.— N —307.7° C.— I 2-(4'-cyano-3',5'-difluorophenyl)-5-[4'-(trans-4''-hexylcyclohexyl) phenyl] pyrimidine
2-(4'-cyano-3',5'-difluorophenyl)-5-[4'-(trans-4''-heptylcyclohexyl) phenyl] pyrimidine
2-(4'-cyano-3',5'-difluorophenyl)-5-[4'-(trans-4''-octylcyclohexyl) phenyl] pyrimidine
2-(4'-cyano-3',5'-difluorophenyl)-5-[4'-(trans-4''-nonylcyclohexyl) phenyl] pyrimidine
2-(4'-cyano-3',5'-difluorophenyl)-5-[4'-(trans-4''-decylcyclohexyl) phenyl] pyrimidine

EXAMPLE 4

Preparation of 2-(4'-fluorophenyl)-5-[4'-(trans-4''propylcyclohexyl) phenyl] pyrimidine:

Step 1 to Step 6:
1-dimethylamino-3-dimethylimino-2-[4'-(trans-4''-propylcyclohexyl)phenyl]-1-propene perchlorate was prepared in the same manner as in Steps 1 through 6 of Example 1.

Step 7:
50 g (0.41 mol) of 4-fluorobenzonitrile was dissolved in 82 cm$^3$ of anhydrous ethanol and 103 cm$^3$ of benzene, cooled with ice and saturated with hydrogen gas. The mixture was maintained at a temperature below 5° C. for one day and night. The solvent was distilled off and the residue was recrystallized from 100 cm$^3$ of ethanol to yield 83 g (0.41 mol) of 4-fluorobenzimidate hydrogen chloride.

Step 8:
310 cm$^3$ of ethanol saturated with ammonia was added to 83 g (0.41 mol) of 4-fluorobenzimidate hydrogen chloride and stirred at room temperature for one day and night. Approximately half of the ethanol was distilled off and the residue was recrystallized to yield 70 g (0.40 mol) of 4-fluorobenzamidine hydrogen chloride.

Step 9:
0.7 g (0.03 mol) of sodium was dissolved in 100 cm$^3$ of methanol. 4.3 g (0.01 mol) of 3-dimethylamino-1-dimethylimino-2-[ 4'-(trans-4''-propylcyclohexyl)phenyl]-2-propene perchlorate and 2.6 g (0.15 mol) of 4-fluorobenzamidine hydrogen chloride were added to the solution and the solution was allowed to sit at a temperature of 60° C. for 5 hours. The product of the reaction was cooled to −20° C. and the crystals were filtered out and washed with water. The crystals were treated through a silica gel column using chloroform as the solvent and recrystallized from a solvent mixture of chloroform and acetone to yield 3.2 g (0.009 mol) of 2-(4'-fluorophenyl)-5-[4-(trans-4''-propylcyclohexyl)phenyl]pyrimidine.

The phase transition temperature of the compound, measured by DSC, was:

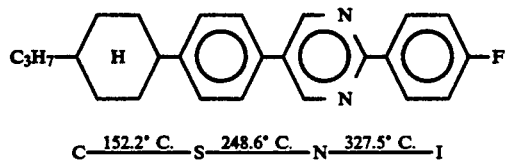

C —152.2° C.— S —248.6° C.— N —327.5° C.— I wherein C is the crystal phase, S is the smectic phase, N is the nematic phase and I is the isotropic liquid phase.

The following are other examples of compounds prepared in accordance with the invention following the procedures of Example 4:

2-(4'-fluorophenyl)-5-[4'-(trans-4''-methylcyclohexyl)phenyl] pyrimidine
2-(4'-fluorophenyl)-5-[4'-(trans-4''-ethylcyclohexyl)phenyl] pyrimidine

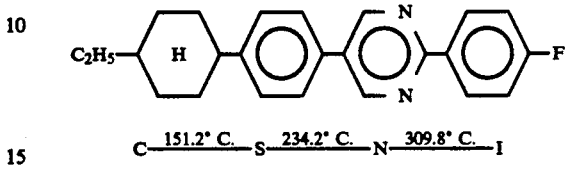

C —151.2° C.— S —234.2° C.— N —309.8° C.— I 2-(4'-fluorophenyl)-5-[4'-(trans-4''-butylcyclohexyl)phenyl] pyrimidine

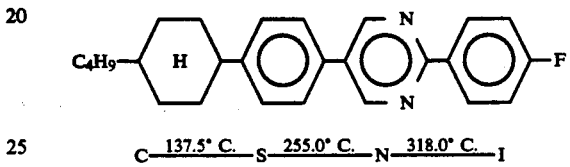

C —137.5° C.— S —255.0° C.— N —318.0° C.— I 2-(4'-fluorophenyl)-5-[4'-(trans-4''-pentylcyclohexyl)phenyl] pyrimidine

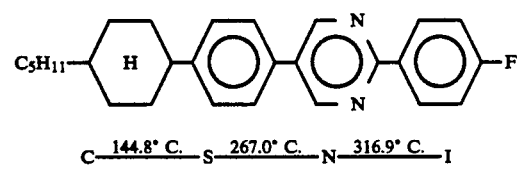

C —144.8° C.— S —267.0° C.— N —316.9° C.— I 2-(4'-fluorophenyl)-5-[4'-(trans-4''-hexylcyclohexyl)phenyl] pyrimidine
2-(4'-fluorophenyl)-5-[4'-(trans-4''-heptylcyclohexyl)phenyl] pyrimidine
2-(4'-fluorophenyl)-5-[4'-(trans-4''-octylcyclohexyl)phenyl] pyrimidine
2-(4'-fluorophenyl)-5-[4'-(trans-4''-nonylcyclohexyl)phenyl] pyrimidine
2-(4'-fluorophenyl)-5-[4'-(trans-4''-decylcyclohexyl)phenyl] pymimidine

EXAMPLE 5

Preparation of 2-(3',4'-difluorophenyl)-5-[4'-(trans-4''-propylcyclohexyl)phenyl]pyrimidine:

Step 1 to Step 6:
1-dimethylamino-3-dimethylimino-2-[4'-(trans-4''-propylcyclohexyl)phenyl]-1-propene perchlorate was prepared in the same manner as in Steps 1 through 6 of Example 1.

Step 7:
50 g (0.36 mol) of 3',4'-difluorobenzonitrile (manufactured by Aldorich Co.) was dissolved in a solution of 72 cm$^3$ of ethanol and 90 cm$^3$ of benzene. The solution was cooled with ice water and saturated with HCl gas dried with concentrated H$_2$SO$_4$. The reaction vessel was tightly sealed and left at a temperature below 5° C. for two days. The solvent was distilled off under reduced pressure over a warm water bath at a temperature below 50° C. The residue was recrystallized from 80 cm$^3$ of methanol to yield 80 g (0.36 mol) of 4-difluorobenzimidate hydrogen chloride.

Step 8:

250 cm³ of ethanol was cooled with ice water and ammonia gas was supplied from a gas cylinder to form an ammonia saturated ethanol solution. The solution was added to 80 g (0.36 mol) of 4-difluorobenzimidate hydrogen chloride and stirred at room temperature overnight. The ammonium chloride (NH₄Cl) deposited was filtered out and about one-half of the volume of ethanol in the filtrate was distilled off on a warm water bath. The residue was recrystallized to yield 68 g (0.35 mol) of 3,4-difluorobenzamidine hydrogen chloride.

Step 9:

0.7 g (0.03 mol) of sodium was dissolved in 100 cm³ of methanol. 4.3 g (0.01 mol) of 3-dimethylamino-1-dimethylimino-1-[4'-(trans-4''-propylcyclohexyl)phenyl]-2-propene and 3.9 g (0.015 mol) of 3,4-bromobenzamidine hydrogen chloride were added to the solution and the solution was allowed to sit on a warm water bath at a temperature of 60° C. for 5 hours. The reaction product was cooled to −20° C. and the crystals formed were filtered out and washed with water. The crystals were recrystallized from a solvent mixture of chloroform and acetone to yield 3.3 g (8.5 mol) of 2-(3',4'-difluorophenyl)-5-[4'-(trans-4'-propylcyclohexyl)phenyl] pyrimidine. The phase transition temperature of this compound, measured by DSC, was:

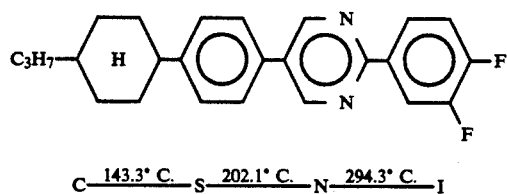

C —143.3° C.— S —202.1° C.— N —294.3° C.— I

The following are other examples of compounds prepared in accordance with the invention following the procedures of Example 5:

2-(3',4'-difluorophenyl)-5-[4'-(trans-4''-methylcyclohexyl)phenyl] pyrimidine 2-(3',4'-difluorophenyl)-5-[4'-(trans-4''-ethylcyclohexyl)phenyl] pyrimidine

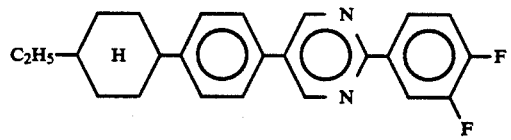

C —144.5° C.— S —190.7° C.— N —271.7° C.— I 2-(3',4'-difluorophenyl)-5-[4'-(trans-4''-butylcyclohexyl)phenyl] pyrimidine

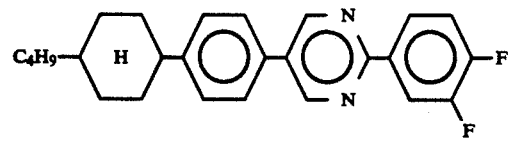

C —102.1° C.— $S_1$ —132.8° C.— $S_2$ —210.6° C.— N —286.7° C.— I wherein $S_1$ and $S_2$ are the smectic phase.

2-(3',4'-difluorophenyl)-5-[4'-(trans-4''-pentylcyclohexyl)phenyl] pyrimidine

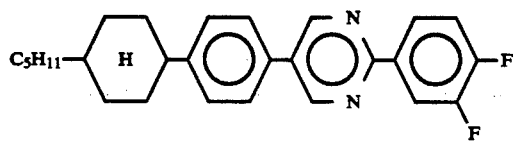

C —114.5° C.— $S_1$ —127.5° C.— $S_2$ —227.5° C.— N —287.7° C.— I 2-(3',4,-difluorophenyl)-5-[4'-(trans-4''-hexylcyclohexyl)phenyl] pyrimidine 2-(3',4'-difluorophenyl)-5-[4'-(trans-4''-heptylcyclohexyl)phenyl] pyrimidine 2-(3',4'-difluorophenyl)-5-[4'-(trans-4''-octylcyclohexyl)phenyl] pyrimidine 2-(3',4'-difluorophenyl)-5-[4'-(trans-4''-nonylcyclohexyl)phenyl] pyrimidine 2-(3',4'-difluorophenyl)-5-[4'-(trans-4''-decylcyclohexyl)phenyl] pyrimidine

COMPOSITION EXAMPLE 1

Several liquid crystal compositions [A1-A5] were prepared by including 10 wt % of a 2-phenyl-5-(4'-trans-cyclohexyl) phenyl pyrimidine derivative in a commercially available liquid crystal composition ZLI-1565 (manufactured by Merck Inc.). Comparative Examples [B1-B2] were prepared by including 10 wt % of $C_5H_{11}$—O—O—O—CN and $C_5H_{11}$—H—O—O—CN, respectively, in ZLI-1565. Comparative Example [B3] was prepared by including 100 wt % ZLI-1565.

The compositions were sealed in 9 μm TN type cells. The N-I Point and $V_{th}$ were measured. The results are shown in Table 3.

TABLE 3

| Compound | N-I Point (°C.) | | $V_{th}$ |
|---|---|---|---|
| A1 ZLI-1565 | 90 | 111 | 2.49 |
|  | 10 | | |
| A2 ZLI-1565 | 90 | 108 | 2.37 |

TABLE 3-continued

| Compound | | N-I Point (°C.) | $V_{th}$ |
|---|---|---|---|
| | 10 | | |
| C₃H₇―〈H〉―〈○〉―〈○〉―〈○〉―CN with F | | | |
| A3 ZLI-1565 | 90 | 104 | 2.12 |
| | 10 | | |
| C₃H₇―〈H〉―〈○〉―〈○〉―〈○〉―CN with F, F | | | |
| A4 ZLI-1565 | 90 | 105 | 2.56 |
| | 10 | | |
| C₃H₇―〈H〉―〈○〉―〈○〉―〈○〉―F | | | |
| A5 ZLI-1565 | 90 | 103 | 2.46 |
| | 10 | | |
| C₃H₇―〈H〉―〈○〉―〈N=N〉―〈○〉―F with F | | | |
| B1 ZLI-1565 | 90 | 101 | 2.51 |
| | 10 | | |
| C₅H₁₁―〈○〉―〈○〉―〈○〉―CN | | | |
| B2 ZLI-1565 | 90 | 99 | 2.47 |
| | 10 | | |
| C₅H₁₁―〈H〉―〈○〉―〈○〉―CN | | | |
| B3 ZLI-1565 | 100 | 87 | 2.43 |

The compositions prepared in accordance with the invention have been described in detail with reference to ZLI-1565. However, it is understood that the increase in the N-I Point and the decrease in $V_{th}$ can be obtained with other compatible liquid crystal compositions. The 2-phenyl-5-(4'-trans-cyclohexyl) phenyl pyrimidine derivatives are included in the composition in at least a minimum effective amount to increase the N-I Point and decrease the threshold voltage as desired and may be included up to about 30 wt % based on the total weight of the composition. Preferably, between about 3 and 20 wt % of the pyrimidine is added to the liquid crystal composition and most preferably about 7.5 to 12.5 wt %.

As described above, the 2-phenyl-5-(4'-trans-cyclohexyl) phenyl pyrimidine derivatives prepared in accordance with the invention have high N-I Points and low threshold voltages. Liquid crystal compositions having a wide temperature range for practical use and low driving voltages are obtained when liquid crystal compounds in accordance with the invention are mixed with conventional liquid crystal compositions. Thus, the pyrimidine derivatives prepared in accordance with the invention are extremely useful as constituent components for nematic liquid crystal compositions.

It will thus be seen that the objects set forth, among those made apparent from the preceding description, are efficiently obtained and, since certain changes may be made in carrying out the above embodiments and in the composition set forth, without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention, which is a matter of language might be said to fall therebetween.

Particularly it is to be understood that in said claims, ingredients or compound recited in the singular are intended to include compatible mixtures of such ingredients wherever the sense permits.

What is claimed is:

1. A 2-phenyl-5-(4'-transcyclohexyl) phenyl pyrimidine derivative represented by the general formula:

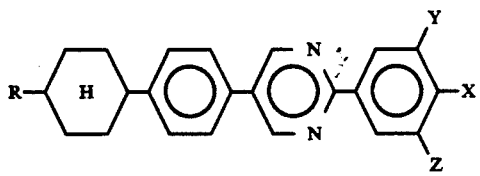

wherein R is a straight chain alkyl group having 1 to 10 carbon atoms; X is CN or F; Y is F or H; Z is F or H; when X is F, one of Y and Z is H and the other is F; when X is CN, at least one of Y and Z is F; and the cyclohexane ring is a trans isomer.

2. The 2-phenyl-5-(4'-trans-cyclohexyl) phenyl pyrimidine derivative of claim 1, wherein X is CN; and one of Y and Z is F and the other of Y and Z is H represented by the formula:

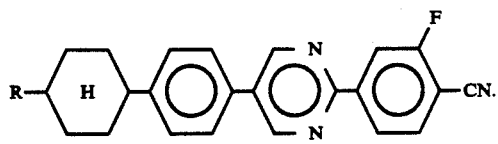

3. Trans-2-(4'-cyano-3'-fluorophenyl)-5(4'-(trans-4"-propylcyclohexyl) phenyl) pyrimidine represented by the formula:

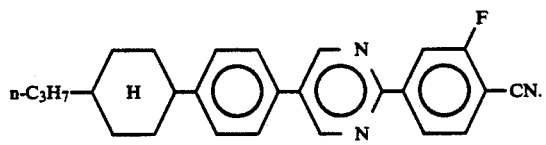

4. The 2-phenyl-5-(4'-trans-cyclohexyl) phenyl pyrimidine derivative of claim 1, wherein X is CN; and Y and Z are F represented by the formula:

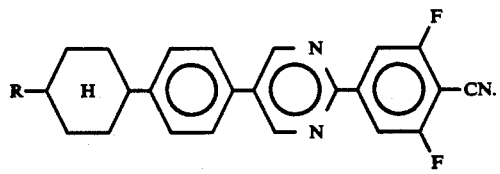

5. Trans-2-(4'-cyano-3',5'-fluorophenyl)-5-(4'-(trans-4"-propylcyclohexyl) phenyl) pyrimidine represented by the formula:

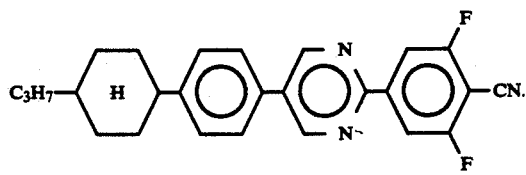

6. The 2-phenyl-5-(4'-trans-cyclohexyl) phenyl pyrimidine derivative of claim 1, wherein X is F; and one of Y and Z is F and the other of Y and Z is H represented by the formula:

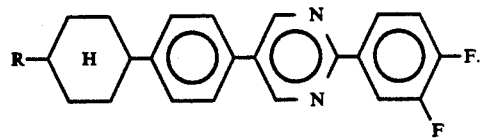

7. Trans-2-(3',4'-difluorophenyl)-5-(4'-(trans-4"-propylcyclohexyl) pheny) pyrimidine represented by the formula:

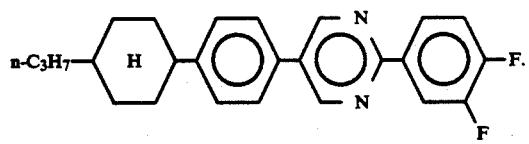

8. The 2-phenyl-5-(4'-trans-cyclohexyl) phenyl pyrimidine derivative of claim 1, wherein the number of carbon atoms in R is 3,4 or 5.

9. The 2-phenyl-5-(4'-trans-cyclohexyl) phenyl pyrimidine derivative of claim 8, wherein the number of carbon atoms in R is 4.

10. A liquid crystal composition comprising an effective amount of at least one 2-phenyl-5-(4'-trans-cyclohexyl) phenyl pyrimidine derivative for widening the nematic temperature range and decreasing the threshold voltage, the pyrimidine derivative having the general formula:

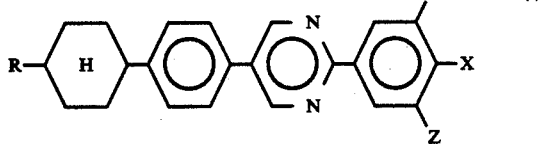

wherein R is a straight chain alkyl group having 1 to 10 carbon atoms; X is CN or F; Y is F or H; Z is F or H; when X is F, one of Y and Z is H and the other is F; when X is CN, at least one of Y and Z is F; and the cyclohexane ring is a trans isomer.

11. The liquid crystal composition of claim 10, wherein the pyrimidine derivative is present between about 1 and 30 wt % based on the total weight of the composition.

12. The liquid crystal composition of claim 11, wherein the pyrimidine derivative is present between about 3 and 20 wt % based on the total weight of the composition.

13. The liquid crystal composition of claim 10, wherein in the 2-phenyl-5-(4'-trans-cyclohexyl) phenyl pyrimidine derivative X is CN; and one of Y and Z is F and the other of Y and Z is H.

14. The liquid crystal composition of claim 13, wherein the 2-phenyl-5-(4'-trans-cyclohexyl) phenyl pyrimidine derivative is 2-(4'-cyano-3'-fluorophenyl)-5-(4'-(trans-4''-propylcyclohexyl) phenyl) pyrimidine.

15. The liquid crystal composition of claim 10, wherein in the 2-phenyl-5-(4'-trans-cyclohexyl) phenyl pyrimidine derivative X is CN; and Y and Z are F.

16. The liquid crystal composition of claim 15, wherein the 2-phenyl-5-(4,'-trans-cyclohexyl) phenyl pyrimidine derivative is 2-(4'-cyano-3',5'difluorophenyl)-5-(4'-(trans-4''-propylcyclohexyl) phenyl) pyrimidine.

17. The liquid crystal composition of claim 10, wherein in the 2-phenyl-5-(4'-trans-cyclohexyl) phenyl pyrimidine derivative X is F; and one of Y and Z is F and the other of Y and Z is H.

18. The liquid crystal composition of claim 17, wherein the 2-phenyl-5-(4'-trans-cyclohexyl) phenyl pyrimidine derivative is 2-(3',4'-difluorophenyl)-5-(4'-(trans-4''-propylcyclohexyl) phenyl) pyrimidine.

19. The liquid crystal composition of claim 10, wherein in the 2-phenyl-5-(4'-trans-cyclohexyl) phenyl pyrimidine derivative the number of carbon atoms in R is 3, 4 or 5.

20. The liquid crystal composition of claim 19, wherein in the 2-phenyl-5-(4'-trans-cyclohexyl) phenyl pyrimidine derivative the number of carbon atoms is 4.

* * * * *